(12) United States Patent
Medoff (10) Patent No.: US 11,490,906 B2
(45) Date of Patent: Nov. 8, 2022

(54) DRILL GUIDES AND INSERTERS FOR BONE PLATES HAVING HOOK MEMBERS

(71) Applicant: Robert J. Medoff, Kailua, HI (US)

(72) Inventor: Robert J. Medoff, Kailua, HI (US)

(73) Assignee: TRIMED INCORPORATED, Santa Clarita, CA (US)

( * ) Notice: Subject to any disclaimer, the term of this patent is extended or adjusted under 35 U.S.C. 154(b) by 247 days.

(21) Appl. No.: 16/869,272

(22) Filed: May 7, 2020

(65) Prior Publication Data

US 2020/0261101 A1     Aug. 20, 2020

Related U.S. Application Data

(63) Continuation of application No. 14/534,613, filed on Nov. 6, 2014, now abandoned.

(Continued)

(51) Int. Cl.
*A61B 17/17* (2006.01)
*A61B 17/92* (2006.01)
(Continued)

(52) U.S. Cl.
CPC ........ *A61B 17/1728* (2013.01); *A61B 17/809* (2013.01); *A61B 17/8014* (2013.01);
(Continued)

(58) Field of Classification Search
CPC ............ A61B 17/1728; A61B 17/1782; A61B 17/92; A61B 17/808; A61B 17/809;
(Continued)

(56) References Cited

U.S. PATENT DOCUMENTS

| 414,311 A | 11/1889 | Haussmann |
|---|---|---|
| 1,338,376 A | 4/1920 | Kocha |

(Continued)

FOREIGN PATENT DOCUMENTS

| DE | 8401092 U1 | 4/1984 |
|---|---|---|
| DE | 102007045885 A1 | 4/2009 |

(Continued)

OTHER PUBLICATIONS

English translation of description of FR-1443965. (Year: 2017).*

(Continued)

*Primary Examiner* — Amy R Sipp
(74) *Attorney, Agent, or Firm* — Patzik, Frank & Samotny Ltd.

(57) ABSTRACT

A system for assisting a surgeon in implanting hook plate-type bone plates includes a cannulated multiple barreled drill guide, a cannulated inserter/impactor, and a cannulated fastener coupling the inserter/impactor to a bone plate. The multiple barreled drill guide facilitates the drilling of at least two parallel holes at the distal end of a bone at the correct position and angle of entry, and includes a body and two drill guide channels coupled to the body in substantially parallel orientation relative to each other, with a guide pin aperture disposed between and substantially parallel to the drill guide tubes. The inserter/impactor likewise includes a central channel accommodating the same guide pin employed to place and align the multiple barreled drill guide.

13 Claims, 7 Drawing Sheets

Related U.S. Application Data (60) Provisional application No. 61/901,964, filed on Nov. 8, 2013.

(51) Int. Cl.
*A61B 17/80* (2006.01)
*A61B 17/00* (2006.01)

(52) U.S. Cl.
CPC .......... *A61B 17/8061* (2013.01); *A61B 17/92* (2013.01); *A61B 17/808* (2013.01); *A61B 2017/0046* (2013.01)

(58) Field of Classification Search
CPC ........ A61B 17/82–826; A61B 2017/90; A61B 2017/922; A61B 2017/046
See application file for complete search history.

(56) References Cited

U.S. PATENT DOCUMENTS

| | | | |
|---|---|---|---|
| 4,201,213 A | 5/1980 | Townsend | |
| 4,565,193 A * | 1/1986 | Streli | A61B 17/809 606/67 |
| 5,385,570 A | 1/1995 | Chin et al. | |
| 5,586,985 A | 12/1996 | Putnam | |
| 6,755,831 B2 | 6/2004 | Putnam | |
| 7,037,308 B2 | 5/2006 | Medoff | |
| 7,267,678 B2 | 9/2007 | Medoff | |
| 7,338,497 B2 | 3/2008 | Coon | |
| 8,177,822 B2 | 5/2012 | Medoff | |
| 8,282,645 B2 | 10/2012 | Lawrence | |
| 3,821,508 A1 | 9/2014 | Medoff | |
| 2003/0040748 A1* | 2/2003 | Aikins | A61B 17/92 606/70 |
| 2004/0092947 A1 | 5/2004 | Foley | |
| 2005/0010228 A1 | 1/2005 | Medoff | |
| 2009/0082770 A1 | 3/2009 | Worner | |
| 2010/0100138 A1 | 4/2010 | Reynolds | |
| 2011/0178524 A1 | 7/2011 | Lawrence | |
| 2011/0213420 A1 | 9/2011 | Medoff | |
| 2011/0276097 A1 | 11/2011 | Raven, III | |
| 2012/0010667 A1 | 1/2012 | Eglseder | |
| 2013/0046314 A1 | 2/2013 | Medoff | |
| 2013/0046349 A1 | 2/2013 | Medoff | |

FOREIGN PATENT DOCUMENTS

| | | | | |
|---|---|---|---|---|
| FR | 1443965 A * | 7/1966 | ......... | A61B 17/1721 |
| FR | 1443965 A | 7/1966 | | |
| FR | 2721195 A1 * | 12/1995 | ............ | A61B 17/15 |
| FR | 2721195 A1 | 12/1995 | | |
| WO | WO 03047416 A2 | 6/2003 | | |

OTHER PUBLICATIONS

English translation of description of FR-2721195. (Year: 2017).*
European Patent Office, European Search Report issued in European Patent Application No. EP13275194, dated Dec. 19, 2013.
European Patent Office, European Search Report issued in European Patent Application No. EP13275195, dated Dec. 20, 2013.
English Translation of German Publication No. DE8401092 (OSCOBAL AG), Published Apr. 5, 1984.
Zuelzer, Wilhelm A., Fixation of Small But Important Bone Fragments With a Hook Plate, The Journal of Bone & Joint Surgery, 1951; 33:430-436.
Weseley, M.S., et al., The Use of the Zuelzer Hook Plate in Fixation of Olecranon Fractures, The Journal of Bone & Joint Surgery, 1976; 58:859-863.
Surgical Technique SCS Volar Distal Radius Plate System, Small Bone Innovations, Inc. Morrisville, Pennsylvania and SBi International, SAS, Peronnas, France, 2006.
Volar Bearing Plate Surgical Technique, TriMed, Inc., Valencia, California, 2011.
LCP Hook Plate 3.5. The Simple Fixation System for Tension Band Plating, Technique Guide, Synthes, Inc., West Chester, Pennsylvania, Jun. 2009.
European Patent Office, European Search Report issued in European Patent Application No. EP14192126, dated Jul. 10, 2015.
English Translation of Description of FR-1443965.
English Translation of Description FR-2721195.

* cited by examiner

DRILL GUIDES AND INSERTERS FOR BONE PLATES HAVING HOOK MEMBERS

CROSS-REFERENCE TO RELATED APPLICATIONS

This application is a continuation of U.S. patent application Ser. No. 14/534,613, filed Nov. 6, 2014, which claims the benefit of provisional U.S. Patent Application Ser. No. 61/901,964, filed Nov. 8, 2013, the entirety of both of which are hereby incorporated by reference.

BACKGROUND OF THE INVENTION

1. Field of the Invention

The present invention relates, in general, to the fixation of bone fractures and, more particularly, to the fixation of bone fractures having small fragments proximate a terminal end of a bone.

2. Description of Related Art

Plates and screws are well accepted techniques for fixation of fractures. The standard bone plate is a planar bar of material, usually metal, having circular and/or slotted holes through which bone screws are placed. The bone plate is used to span a fracture and fixation screws are placed through holes in the bone plate positioned on either side of the fracture to secure the bone fragments the plate.

One example of a fracture occurring relatively close to the end of a bone is a fracture of the lateral malleolus, the terminal portion of the fibula that is present on the outside of the ankle, occurring close to its tip. In such situations, only a very small distal fragment may be present, providing inadequate room for more than one or two screws to be placed. Moreover, since the deep portion of this bone is a part of the overall ankle joint, screws cannot be placed through both cortices, as is commonly practice with plate/screw techniques.

Distal radius fractures (what is often meant when using the term 'wrist fracture') are common injuries. These fractures are often comminuted and unstable. It is of importance in addressing such fractures to restore a smooth, anatomic and congruent articular surface with enough stability so that it does not displace during healing. In other locations in the body one objective of internal fixation is to produce compression between stable and unstable fragments in order to promote healing. However, in the case of the distal radius fractures, fixation that would produce this type of compressive loads between the articular fragments and the shaft may result in migration of the fragments, loss of length, malunions and failure. For this reason, the tenets of internal fixation for distal radius fractures are different, aimed at achieving a stable anatomic reduction while maintaining the joint surface in space supported out to length.

Generally volar fixation plates need to be thick in cross-section in order to provide sufficient material to allow enough internal threads in the holes in order to securely lock the cooperatively threaded peg to the plate (whether at a fixed or variable angle). Since it is known that thick implants close to the rim of the distal radius may often cause irritation and even rupture of important tendons and other vital structures nearby, existing volar generally plates do not extend to the distal rim. As a result, small fractures of the distal volar rim are often not secured by these plate designs, which can result in the fragment flipping over the edge of the plate, potentially causing catastrophic loss of reduction and dislocation of the carpal bones of the wrist.

Hook plates are implants that have been used at other locations to address fixation of a small terminal fragment with little available osseous bone area to accommodate fixation screws. Although early designs such as the LCP Hook Plate manufactured by Synthes, Inc. wrap around the end of the bone, these types of implants do not achieve any internal purchase of the fragment to be secured, and may have very limited to no purchase overall, resulting in poor rotational stability and limited resistance to sideways drift of the terminal fragment.

The hook plates disclosed within U.S. Pat. No. 8,177,822 to Medoff, the entirety of which is hereby incorporated by reference, are configured for application to the lateral malleolus or the olecranon, and achieve fixation of terminal fragments with two intra-osseous 'teeth', or "hook members", that provide rigid internal purchase of the fragment. These hook plates provide for rigid fixation of the terminal fragment and angular or translational movement under the plate. In addition, this type of plate promotes compressive load across the fracture which is intended for treatment at these locations.

For fixation of the distal radius, however, the configuration of these types of hook plates is not optimal, especially for fractures involving the volar or dorsal rim. Since hook plates such as those disclosed in U.S. Pat. No. 8,177,822, configured for application to the lateral malleolus or the olecranon, promote compression against the stable fragment, in the case of distal radius fixation this would cause shortening of the fragment into the metaphyseal bone, and thus loss of articular reduction. For fractures of the distal radius, radial hook plates, such as those disclosed in U.S. Pat. No. 8,821,508 to Medoff and Shin, the entirety of which are hereby incorporated by reference, are preferred. Moreover, hook plates of a differing design may alternatively be employed to address fractures proximate the terminal ends of the fifth metatarsal bone, the hip, shoulder/clavicle, or other bones.

U.S. Pat. No. 8,177,822 discloses a multi-barreled drill guide for drilling pilot holes for placement of hook plates, including hook plates configured for addressing fractures of the lateral malleolus; and U.S. Pat. No. 8,821,508 discloses holders/impactors for the affixation of hook plates, including hook plates configured for addressing fractures of the distal radius. While these drill guides and holders/impactors are useful, there is a need for an overall system enabling surgeons to more easily and accurately place hook plates for optimal securement of small terminal end bone fragments.

Accordingly, it is an object of the present invention to provide an overall system for the placement of hook plates, that employs the placement of a guide pin, such as a Kirschner, or K-wire, prior to the drilling of pilot holes and the impacting of the hook plate into the bone, as a common basis for the positioning of both associated drill guides and associated inserters/impactors.

It is another object of the present invention to provide a hook plate drill guide and an associated holder/impactor that permit the drilling of pilot holes and the impacting of the hook plate into the bone prior to the removal of the common guide pin that was initially placed through the fracture site.

It is a further object of the present invention to provide an overall system for the placement of hook plates that reduces or eliminates the risk of placing pilot holes, and the hook plates themselves, at an improper position or an improper angle, making the implantation procedure more precise while, at the same time, permitting the procedure to be performed in a minimal amount of time, while requiring the surgeon to perform a minimal amount of steps.

These and other objects and features of the present invention will become apparent in view of the present specification, drawing and claims.

BRIEF SUMMARY OF THE INVENTION

The present invention comprises a system for assisting the surgeon in implanting hook plate-type bone plates, including a cannulated multiple barreled drill guide and a cannulated inserter/impactor. The multiple barreled drill guide facilitates the drilling of at least two parallel holes at the distal end of a bone at the correct position and at the correct angle. In one embodiment, an additional third hole may be provided for a distal cross-locking peg to be placed through the bone. This optional cross-locking peg may be at a position between two hook members of a bone plate. In one embodiment, the multiple barreled drill guide has a body, and two drill tubes extending through the body in substantially parallel orientation relative to each other, with a guide pin aperture disposed either between our outside of and substantially parallel to the drill tubes. The longitudinal axes of the drill tubes and guide pin aperture are angled relative to the longitudinal body of the drill guide in a manner that substantially coincides with the angle between the intra-osseous tines and elongated body of an associated bone plate to be implanted. The multiple barreled drill guide may further include a threaded aperture, threadedly receiving an associated fastener. In one embodiment, the fastener is cannulated and serves to both temporarily attach the inserter/impactor to the hook plate, and to facilitate the drilling of a locking peg pilot hole through the fastener for enhanced subchondral fixation. Like the multiple barreled drill guide, the inserter/impactor includes a channel accommodating the same guide pin employed to place and align the multiple barreled drill guide. The inserter/impactor has a bottom surface contour that substantially corresponds to the top distal surface contour of an adjacent portion of the hook plate upon attachment of the inserter/impactor to the hook plate.

DETAILED DESCRIPTION OF THE INVENTION

While several different embodiments of certain components of the present invention are described herein and shown in the various figures, the use of the prime symbol in conjunction with common reference numerals in the figures denote similar or analogous elements or structure to those of a previously described embodiment.

Figure 12A:
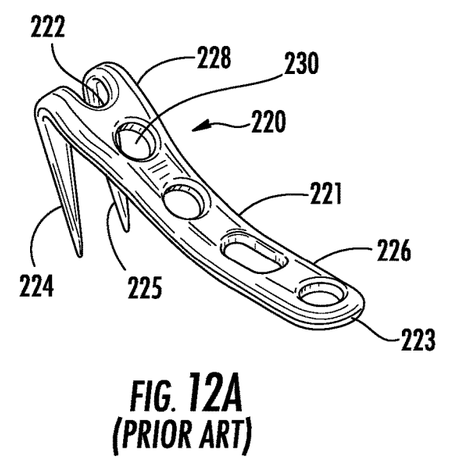
FIG. 12A is top perspective view of a prior art 4-hole, neutral offset fracture fixation plate, configured for volar application in the fixation of certain fractures of the distal radius.
Figure 12B:
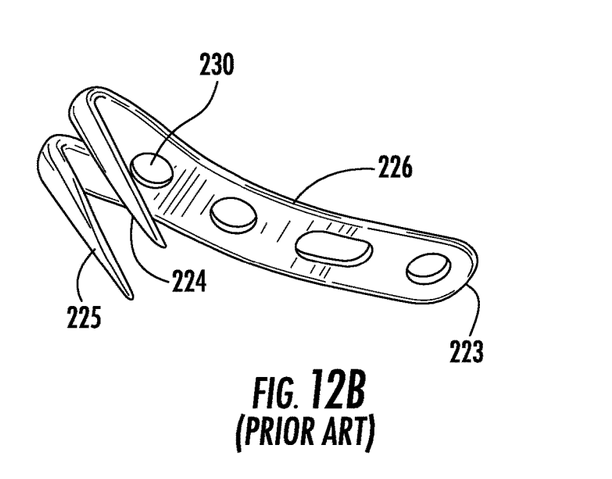
FIG. 12B is a bottom perspective view of the prior art fracture fixation plate of FIG. 12A.

A four-hole, neutral offset bone plate 220, configured for volar application in conjunction with fractures of the distal radius and for which the drill guide and inserter/impactor of FIGS. 1-11 of the present invention may be employed for placement and affixation, is shown in FIGS. 12A and 12B as comprising elongated body 221, having a first end 222 proximate first hook member, or intra-osseous tine 224 and second hook member, or intra-osseous tine 225. Elongated body 221 includes a first region 228 proximate first end 222, a second region 226 proximate a second end 223, and an intermediate, angled, or "flared" region disposed between first region 228 and second region 226. This angled region is generally defined and created by the presence of an angle of curvature relative to the bottom surface of bone plate 220 substantially matching the inclination of the flare of the associated bone requiring fracture fixation.

Elongated body 221 further includes a plurality of apertures extending therethrough for use in conjunction with conventional locking or non-locking bone screws, with three circular holes, including female threaded locking peg hole 230, and one slotted hole. The use of a locking peg placed through locking peg hole 230 and into adjacent bone provides enhanced subchondral fixation directed at an angle that extends between the axes of hook members 224 and 225. This allows a third point of subchondral support in addition to the two hook members, acting like a cup behind the articular surface. The female threads of locking peg hole 230 permit a cannulated set screw to be employed to attach hook plate 220 to a cannulated inserter/impactor.

Figures 13A, 13B:
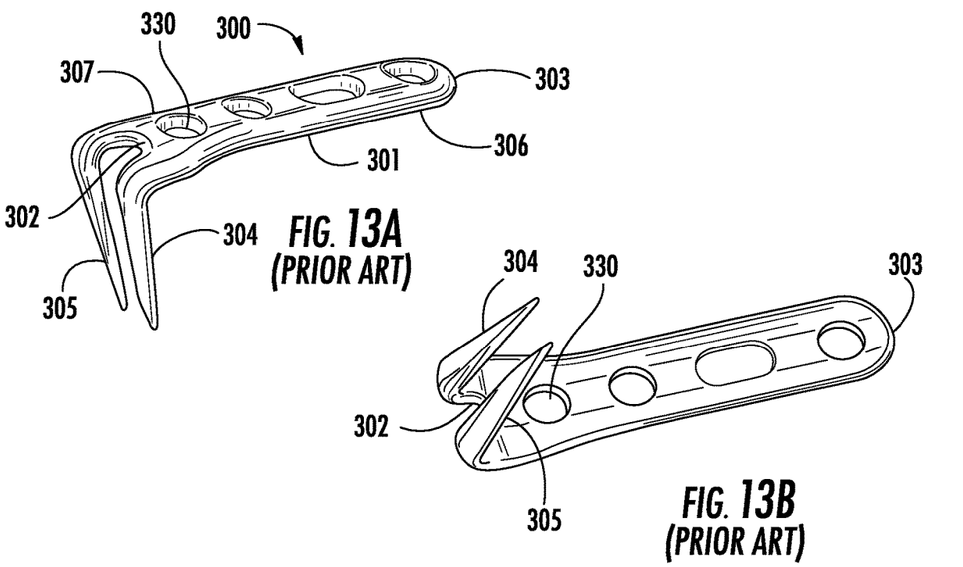
FIG. 13A is top perspective view of a prior art 4-hole, neutral offset fracture fixation plate, configured for dorsal application in the fixation of certain fractures of the distal radius.
FIG. 13B is a bottom perspective view of the prior art fracture fixation plate of FIG. 13A.
Figure 14:
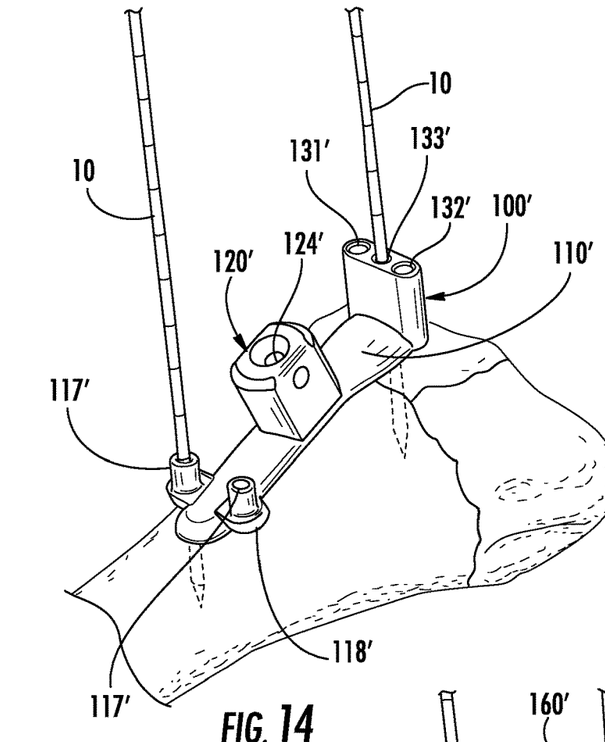
FIG. 14 is a top perspective view of another embodiment of a cannulated, guide wire-accommodating, double barreled drill guide, configured for dorsal application in the fixation of certain fractures of the distal radius, and shown having been slid along an exposed length of a distal guide pin and adjacent a fracture of the distal dorsal rim.
Figure 15:
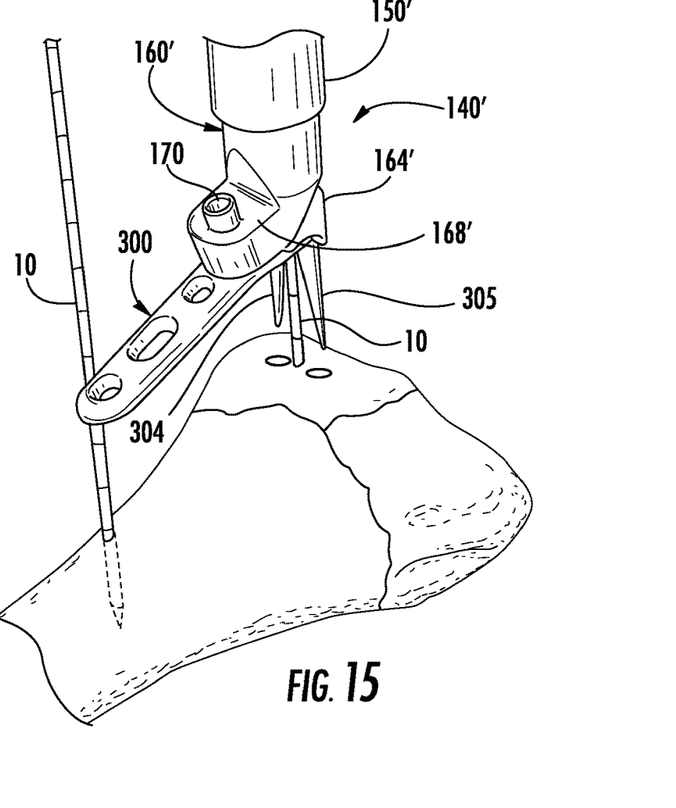
FIG. 15 is a top perspective view of a portion of another embodiment of a cannulated, guide wire accommodating inserter/impactor and associated cannulated fastener, configured for dorsal application in the fixation of certain fractures of the distal radius, shown attached to a fracture fixation plate of FIGS. 13A-13B and after having been slid along an exposed length of a distal guide pin during placement adjacent a fracture of the distal dorsal rim.
Figure 16:
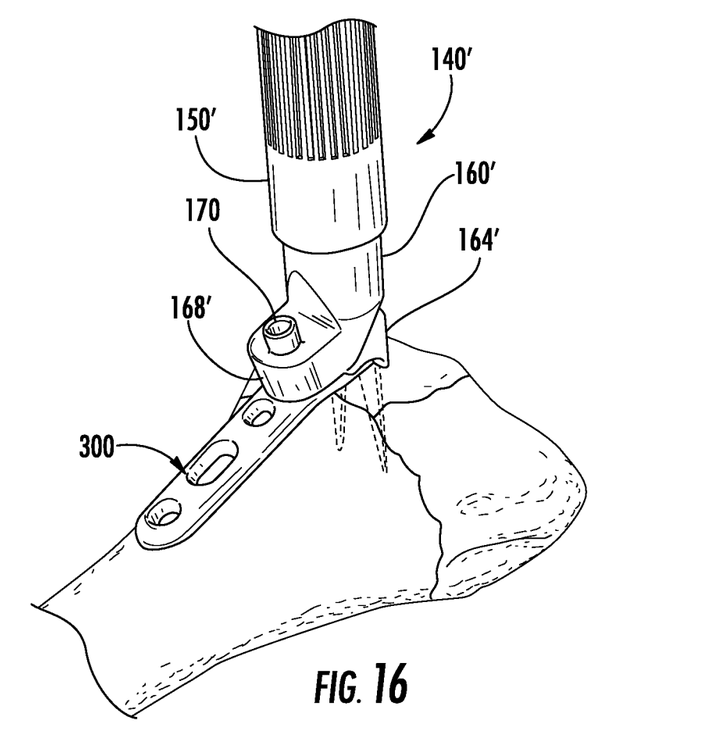
FIG. 16 is a top perspective view of the inserter/impactor, cannulated fastener, and fracture fixation plate of FIG. 15, shown following placement of the intra-osseous tines of the plate through the pilot holes and removal of the guide pins.

Another four-hole, neutral offset bone plate 300, configured for dorsal application in conjunction with fractures of distal radius and for which the drill guide and inserter/impactor of FIGS. 14-16 of the present invention may be employed for placement and affixation, is shown in FIGS. 13A and 13B as comprising elongated body 301, having a first end 302 proximate first hook member, or tooth member 304 and second hook member, or tooth member 305. Elongated body 301 includes a curved apex proximate first end 302, a second region 306 proximate a second end 303, and an intermediate, angled, or "flared" region 307 disposed between the curved apex and second region 306.

Elongated body 301 further includes a plurality of apertures extending therethrough for use in conjunction with conventional locking or non-locking bone screws, including three circular holes, and one slotted hole. The use of a locking peg through locking peg hole 330 and into adjacent bone provides enhanced subchondral fixation directed at an angle that extends between the axes of hook members 304 and 305. This allows a third point of subchondral support in addition to the two hook members, acting like a cup behind the articular surface.

Angled or flared region 307 is generally defined and created by the presence of an angle of curvature relative to the bottom surface of bone plate 300 proximate the juncture of substantially linear first region 301 and substantially linear angled, or flared region 307. The length of the linear angled region 307 and the inclination defined by the angle of curvature substantially match the length and inclination of the flare of the associated bone requiring fracture fixation, in this case the radius, with dorsal application proximate the dorsal rim at the distal radial epiphyseal plate. As a result, the bottom surface of elongated body 301 of bone plate 300 is given an overall longitudinal contour which substantially corresponds to the flared profile of the distal end of the human radius proximate the dorsal rim.

A cannulated, central guide wire-accommodating, double barreled drill guide 100, configured for use in addressing fractures of the volar rim of the distal radius in conjunction with the hook plates of FIGS. 12A and 12B, and in conjunction with the cannulated inserter/impactor of FIGS. 7 through 11, is shown in FIGS. 1 through 6 as comprising elongated body 110, quick connect hub 120, and head region 130. Elongated body 110 comprises proximate end 111, and distal end 112 terminating in head region 130. With cross-reference to FIGS. 12A and 12B, and with the exception of bosses 118 and associated guide pin tubes 117, body 110 has substantially the same configuration and dimensions as elongated body 221 of hook plate 220, with substantially linear region 114 of body 110 being configured substantially similarly to substantially linear region 226 of hook plate 220, with flared region 115 of body 110 being configured substantially similarly to the flared region of hook plate 220, and with bottom surface 116 of body 110 having a curvilinear, contoured shape substantially similar to the curvilinear, contoured bottom surface of elongated body 221 of hook plate 220.

Figure 1:
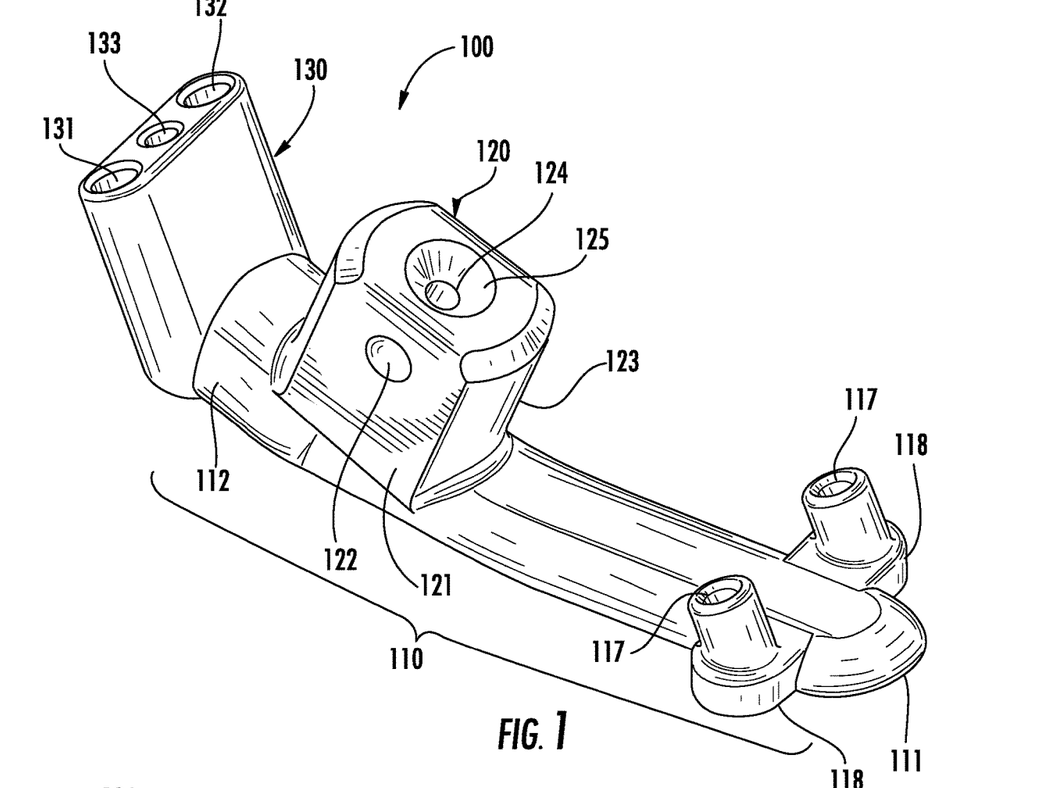
FIG. 1 is a top perspective view of an embodiment of a cannulated, guide wire-accommodating, double barreled drill guide, configured for volar application in the fixation of certain fractures of the distal radius.

Body 110 further comprises two opposing bosses 118 proximate first end 111, each having a guide pin tube 117 sized to accommodate passage of a guide pin therethrough. Upon removal of double barreled drill guide 100 following the drilling of pilot holes for the intra-osseous tines, or hook members of a hook plate, guide pins placed through one or both of guide pin tubes 117 may be left in place, serving as temporary buttresses or locating members to facilitate accurate placement proximally of the hook plate as it is impacted into place and as it is further secured to the bone with suitable fasteners. Additional guide pin tubes may optionally disposed along body 110, likewise sized to permit further guide pins to be placed therethrough, enabling further temporary securement of drill guide 100 in a desired position prior to the drilling of pilot holes for the intra-osseous tines of the hook plate.

Quick connect hub 120 is coupled to body 110 and facilitates the optional connection of a quick release handle 160 to drill guide 100 to further facilitate manual placement of drill guide 100 across a fracture site, if desired. Quick connect hub 120 is generally cube-shaped, with two opposing planar sides 121 and two opposing arcuate sides 122, yielding a horizontal cross-section that is substantially stadium-shaped. Planar sides 121 each have an associated dimpled indent 122 which, in conjunction with the stadium-shaped cross-section of quick connect hub 120, facilitates the attachment of a quick release handle to quick connect hub 120. Quick connect hub 120 further comprises central vertical channel 124, extending through both quick connect hub 120 and body 110, and having an associated countersunk aperture 125 extending through a top surface of quick connect hub 120. Central vertical channel 124 is oriented, relative to body 110, at an angle corresponding to the angle at which a distal locking peg is disposed through locking peg hole 230 of hook plate 220, permitting a K-wire to be initially placed through vertical channel 124 in order to confirm the final position through which a distal locking peg will be placed between the axes of hook members 224 and 225.

Head region 130 of drill guide 100, coupled to body 110 at distal end 112, comprises two substantially parallel drill tubes 131 and 132, with guide pin channel 133 disclosed between and parallel to drill tubes 131 and 132. In a preferred embodiment, drill tubes 131 and 132 are both sized to closely accommodate the passage of a 1.75 millimeter drill bit in order to pre-drill pilot holes to accommodate the intra-osseous tines of hook plate 220, and are spaced apart from each other by a distance substantially corresponding to the distance between intra-osseous tines 224 and 225 of the hook plate to be impacted into a distal bone fragment. The predominantly longitudinal axes of the drill guides are also oriented relative to a predominantly longitudinal axis of body 114 at an angle that substantially corresponds to the angle between the predominantly longitudinal axis of hooks 224 and 225 to the predominantly longitudinal axis of linear portion 226 of plate 220. Alternatively, drill tubes 131 and 132 may of different diameter to accommodate other sizes of drills or pins, or enlarged to permit them to serve as outer sleeves that can accommodate a variety of tubular insert sleeves, each differently sized to accommodate a surgical drill bit having a specific desired diameter.

Guide pin channel 133 is sized to closely accommodate the passage of a guide pin, such as a 1.1 millimeter Kirschner wire, or K-wire, therethrough. As discussed in further detail below, guide pin channel 133 permits a guide pin to initially be placed into the bone at a desired location of the fracture site, with the accuracy of the placement optionally verified by C-arm. The free, proximal end of the guide pin is then advanced through guide pin channel 133 from its bottom opening, by sliding drill guide 100 along the exposed length of the guide pin until arcuate bottom surface 116 of drill guide 100 rests against the surface of the bone proximate the fracture site, and the bottom openings of drill tubes 131 and 132 rest against the distal bone fragment(s) proximate the fracture site. Alternatively, the drill guide may be initially placed in position adjacent the bone, and a K-wire placed through guide pin channel 133 and into the bone, with subsequent optional verification of position using a C-arm.

Figure 2:
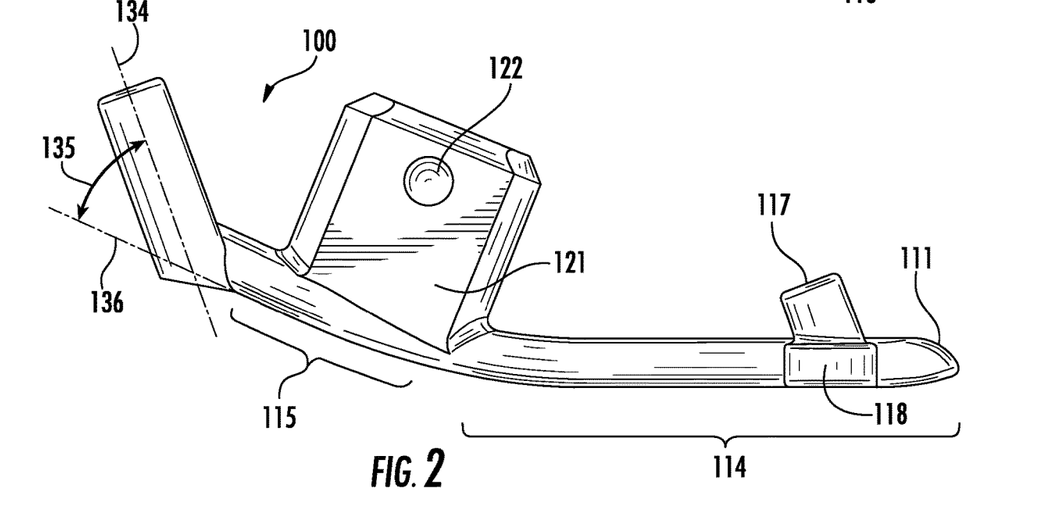
FIG. 2 is a left side view of the drill guide of FIG. 1.
Figure 3:
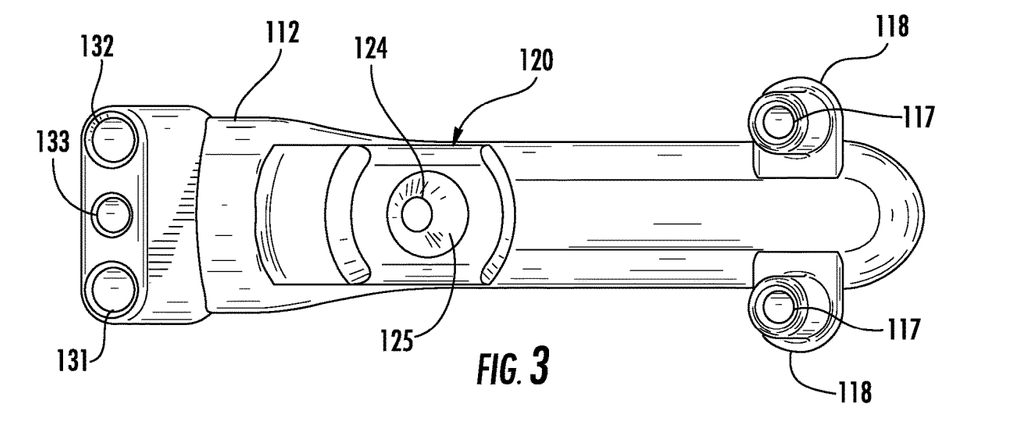
FIG. 3 is a top plan view of the drill guide of FIG. 1.
Figure 4:
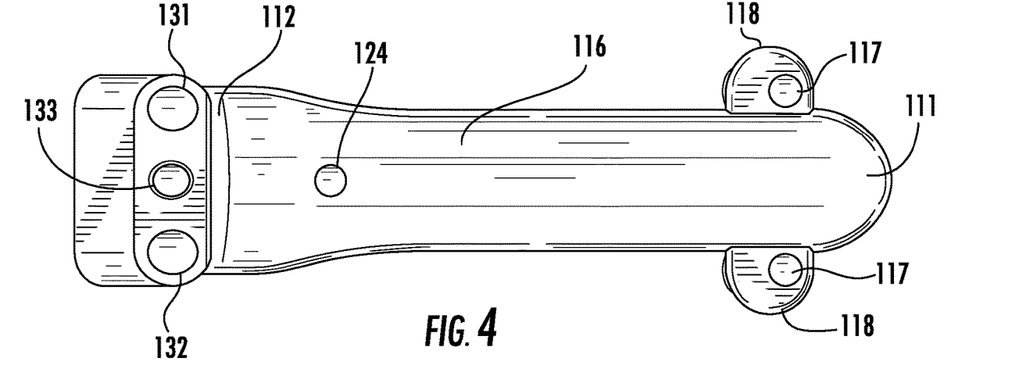
FIG. 4 is a bottom view of the drill guide of FIG. 1.
Figure 5:
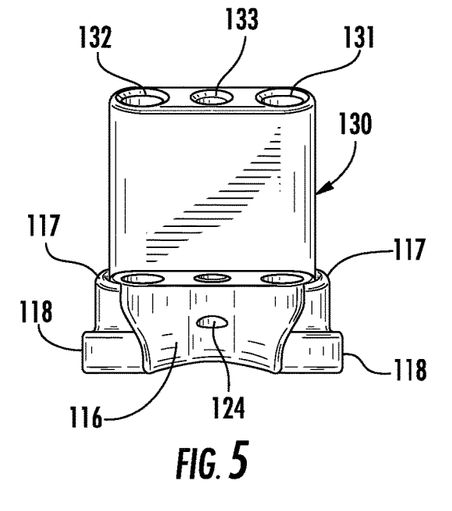
FIG. 5 is a front view of drill guide of FIG. 1.
Figure 6:
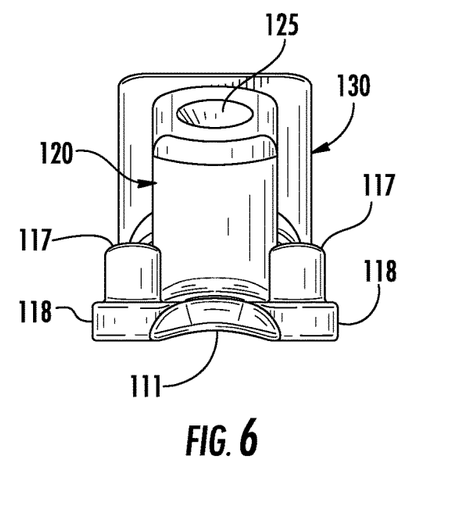
FIG. 6 is a rear view of the drill guide of FIG. 1.

As discussed above, body 110 of drill guide 100 has substantially the same configuration, contour and dimensions as elongated body 221 of hook plate 220. Moreover, as best seen in FIGS. 2, 12A and 12B, the parallel longitudinal axes 134 extending through drill tubes 131 and 132 and guide pin channel 133 are disposed at an angle 135, relative to longitudinal axis 136 of flared region 115 of body 110, that substantially corresponds to the angle between the longitudinal axes of hook members 224 and 225 and the adjacent, flared region of hook plate 220. In this manner, pilot holes drilled through drill tubes 131 and 132 following the positioning of drill guide 100 adjacent the bone, are disposed at an angle, or attitude, that permits body 221 of hook plate 220 to rest flush against the bone upon impacting the intra-osseous tines 224 and 225 of hook plate 220 into the pilot holes.

A first embodiment of a cannulated inserter/impactor 140 of the present invention, configured for use in addressing fractures of the volar rim of the distal radius in association with the drill guide shown in FIGS. 1 through 6 and the hook plate shown in FIGS. 12A and 12B, is shown in FIGS. 7 through 11 as comprising cannulated handle 150, cannulated base 160 and cannulated set screw 170. Although inserter/impactor 140 is show in FIGS. 7 and 8 as being constructed of separate components 150 and 160, in other embodiments these may be combined as a single structure. However, there are certain advantages to the two-piece construction of FIGS. 7 through 11. Specifically, it is desirably for the inserter/impactor to have a handle of sufficient length to provide a gripping region of sufficient size to provide ergonomic use and operation of the inserter/impactor. This desired length is significantly longer than the approximately three centimeters of exposed guide pin length that is to be left after cutting the guide pin following placement of the drill guide, as explained in detail below. Accordingly, a unitary inserter/impactor of having sufficient handle length will not leave an exposed guide pin extending through a top opening. The modular, two-piece construction of the inserter/impactor provides a handle of sufficient ergonomic length while, at the same time, upon separation of the handle, providing sufficient access and clearance to the guide pin to enable a drill to be employed for its removal.

Figure 7:
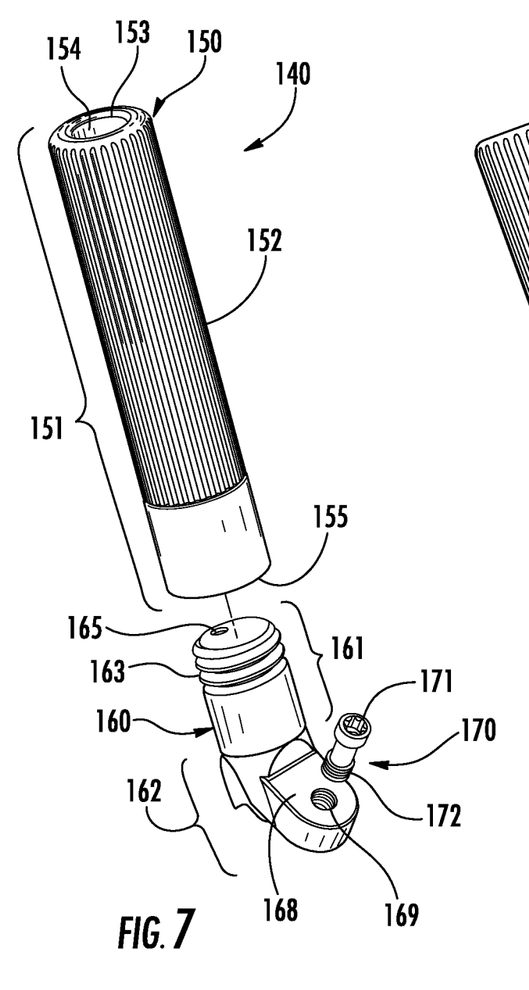
FIG. 7 is an exploded perspective view of an embodiment of a cannulated, guide wire accommodating inserter/impactor and associated cannulated fastener, configured for volar application in the fixation of certain fractures of the distal radius.

Handle 150 is generally cylindrical and hollow tubular in construction, and includes elongated body 151, having a top striking surface 153, bottom end 155, and ribbed or knurled gripping region 152. Channel 154 extends through body 151 from an opening through top surface 153 to an opening through bottom end 155. Top surface 153 of handle 150 serves as a striking surface enabling a hammer to be employed to drive the hook members of a volar bone plate engaged by inserter/impactor 140 into associated pre-drilled pilot holes. A portion of the interior surface of channel 154 adjacent bottom end 155 is internally female threaded and threadedly engages a cooperating, male threaded portion 163 of base 160 for removable attachment of handle 150 to base 160.

Base 160 includes curvilinear bottom surface 164 and flange 168 having set screw aperture 169. Set screw aperture 169 is internally female threaded to threadedly and axially receive male threads 172 of set screw 170 for removable attachment of set screw 170 to base 160, and for overall removable attachment of inserter/impactor 140 to a hook plate such as volar plate 220 of FIGS. 12A and 12B. A cannula, or longitudinal central channel 165, sized in diameter to permit close passage of a guide pin to be extended therethrough, extends longitudinally through the entire length of base 160, from the top surface to bottom surface 164. Upon threaded attachment of handle 150 to base 160, central channel 165 of base 160 communicates with channel or interior region 154 of handle 150.

Set screw 170 includes a cannula, or longitudinal channel extending therethrough, top opening 171, and a shaft region terminating in male external threads 172. The longitudinal channel includes an interior serrated or fluted region adjacent top opening 171 configured for mating engagement with a hexalobular-type or other suitable screwdriver. The shaft of set screw 170 is long enough to permit, upon full threaded advancement of set screw 170 through screw aperture 169 of base 160 until the head of set screw 170 contacts flange 168, for at least a portion of threads 172 to extend through bottom surface 164 of base 160, thereby permitting threads 172 to further threadedly engage locking peg hole 230 of hook plate 220, thereby securing base 160 to hook plate 220.

Upon such securement of base 160 of inserter/impactor 140 to hook plate 220, the predominantly longitudinal axis of the longitudinal channel extending through set screw 170 is positioned at an angle, relative to a predominantly longitudinal axis of the body of hook plate 220 at locking peg hole 230, that is the same as the relative position and angle at which a predominantly longitudinal axis of central vertical channel 124 is positioned relative to a predominantly longitudinal axis of elongated body 110 of drill guide 100. In this manner, and as will be discussed in further detail below, a K-wire or guide pin placed through central vertical channel 124 following placement of drill guide 100 adjacent a fracture site may be used as a guide for reference purposes as an indicator of the position at which a pilot hole for a cross-locking fastener to be placed through locking peg hole 230 may subsequently be drilled through set screw 170 upon the subsequent placement of hook plate 220 at the fracture site.

Upon attachment of inserter/impactor 140 to a hook plate 220 via the threaded engagement of set screw 170 with locking peg hole 230, the contour of curvilinear bottom surface 164 of inserter/impactor base 160 is configured to substantially match the adjacent top surface contours of, and to rest directly atop, a distal portion of hook plate 220, with the apex of hook members 224 and 225 adjacent an arcuate portion of bottom surface 164, and with a longitudinal axis of inserter/impactor 140 being parallel to and proximate to the longitudinal axes of hook members 224 and 225. This, in turn, transfers a striking force applied to top striking surface 153 of inserter/impactor 140 in a direction substantially along the length of both hook members 224 and 225 of attached hook plate 220, to facilitate impacting the hook members into previously drilled pilot holes into one or more bone fragments proximate a fracture site.

Figure 8:
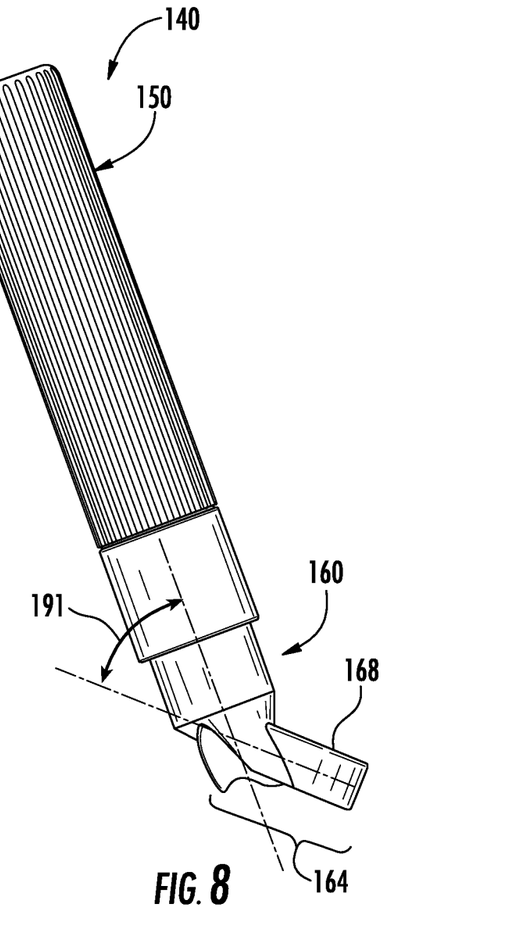
FIG. 8 is a right side view of the inserter/impactor of FIG. 7.
Figure 9:
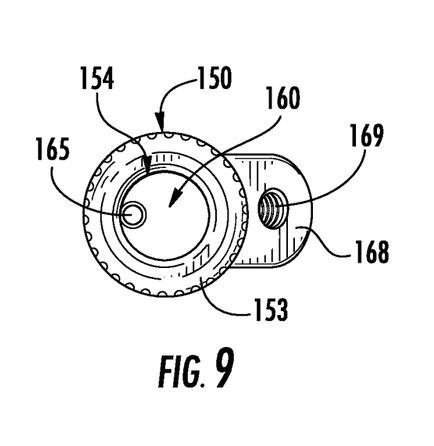
FIG. 9 is a top plan view of the inserter/impactor of FIG. 7.
Figure 10:
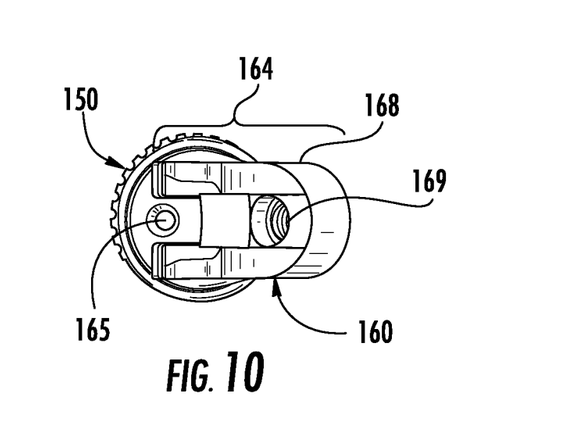
FIG. 10 is a bottom view of the inserter/impactor of FIG. 7.
Figure 11:
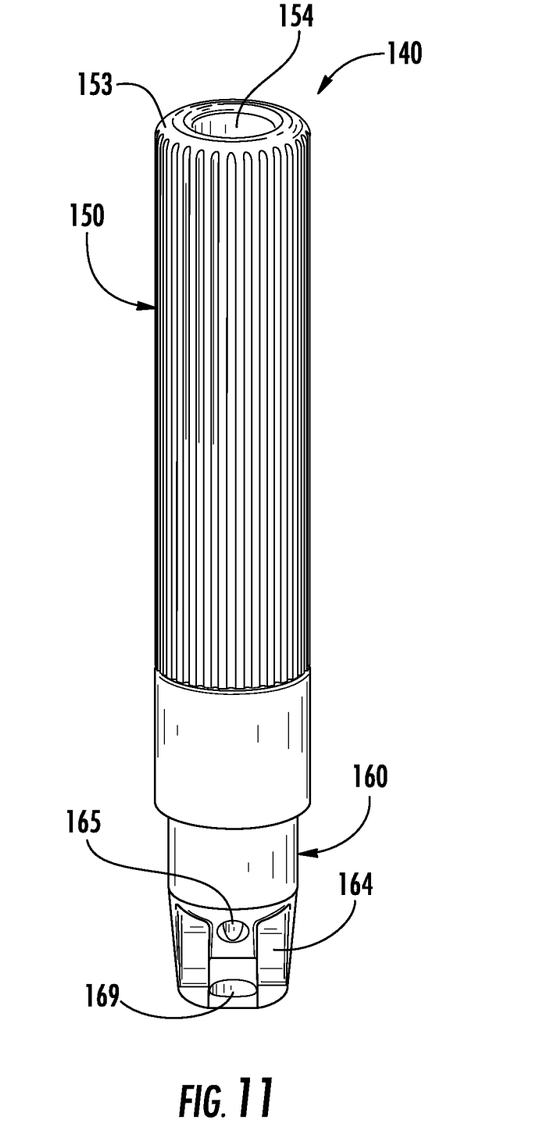
FIG. 11 is a rear view of the inserter/impactor of FIG. 7.

Moreover, with reference to FIG. 8, the longitudinal axis of flange 168 is disposed at an angle 191 relative to the longitudinal axis of elongated body 151 that substantially coincides with the angle between the flared region and hook members 224 and 225 of bone plate 220. Furthermore, with reference to FIG. 2, angle 191 also substantially coincides with angle 135 between longitudinal axis 134 of, collectively, drill tubes 131 and 132 and guide pin channel 133, and longitudinal axis 136 of flared region 115 of drill guide 100. This, in turn, further enables the parallel alignment of a longitudinal axis of body 151 of inserter/impactor 140 with the longitudinal axes of hook members 224 and 225 of bone plate 220 as well as with the longitudinal axes of the pilot holes that are drilled to accept the hook members using drill guide 100.

Notably, inserter/impactor 140, unlike certain prior art inserters, does not require the placement of any portion of the inserter/impactor beneath the bottom surface of an attached bone plate in order to securely hold the bone plate, which requires removal of the inserter/impactor prior to final impaction of the bone plate adjacent the surface of the bone so as to avoid interference caused by intervening structure of the inserter/impactor.

The use of an overall surgical system employing a cannulated drill guide and a cannulated inserter/impactor of the present invention will now be described with reference to FIGS. 14 through 17 using variations of the components previously described, that are instead configured for use in addressing fractures of the dorsal rim of the distal radius in conjunction with the dorsal hook plate of FIGS. 13A and 13B.

First, a skin incision is made ulnar to Lister's tubercle. The dorsal retinacular sheath is excised, followed by dissection of either the 3$^{rd}$ and 4$^{th}$ or 4$^{th}$ and 5$^{th}$ extensor compartments. The extensor pollicis longus is transposed, if necessary, and the fracture is reduced, and temporarily fixed with one or more K-wires, as needed.

Next, cannulated dorsal drill guide 100' is placed in the desired position, as shown in FIG. 14. With cross-reference to FIGS. 13A and 13B, and with the exception of bosses 118' and associated guide pin tubes 117', body 110' of drill guide 100' has substantially the same configuration and dimensions as elongated body 301 of hook plate 300, with a substantially linear region of body 110' being configured substantially similarly to a substantially linear region of hook plate 300, with a flared region of body 110' being configured substantially similarly to the flared region of hook plate 300, and with a bottom surface of body 110' having a surface contour substantially similar to the bottom surface contour of elongated body 301 of hook plate 300.

A quick release handle may optionally be attached to quick connect hub 120' of drill guide 100' to assist in the initial placement of drill guide 100'. Following initial placement of the drill guide, a 1.1 millimeter K-wire 10 is advanced through guide pin channel 133' and into a terminal bone fragment in order to verify the positions on opposing sides of K-wire 10 in which the hook members of a dorsal hook plate are to be impacted. As shown in FIGS. 14 and 15, each K-wire 10 may include alternating stripes of a predetermined length, such as five millimeters, so that, among other things, the depth at which a K-wire is inserted into a bone may be readily gauged, and the length at which a K-wire is to be cut may be readily determined. A C-arm or other medical imaging apparatus is preferably employed to confirm that the position of K-wire 10 is subchondral to the joint and is properly positioned, both distally and angularly.

A second K-wire may optionally be placed through central vertical channel 124' of quick connect hub 120' and advanced into the bone to verify the position where a cross locking peg will subsequently be placed through locking peg hole 330 of dorsal hook plate 300 and into the bone at a position between the hook plate's intra-osseous tines. The proper placement of this second K-wire may likewise be verified by C-arm, if desired. As shown in FIG. 14, additional K-wires 10 may further be placed through one or both of guide pin tubes 117' extending from bosses 118' to function, upon subsequent removal of drill guide 100' over K-wires 10, as guides to facilitate the placement of a dorsal hook plate, proximally.

Next, the distal K-wire 10 extending above vertical channel 124' is cut to extend no more than approximately thirty millimeters, to provide clearance for drill bits to be advanced through drill tubes 131' and 132'. If a K-wire 10 was previously placed through central vertical channel 124' of quick connect hub 120' as described above, this K-wire is removed. A 1.75 millimeter drill bit is then employed to drill holes at a desired depth through drill tubes 131' and 132' as pilot holes for the hook members of a dorsal hook plate, at the position and angle determined by the positioning of head region 130' of drill guide 100', further determined by the positioning and parallel angle of the initially placed K-wire 10. Drill guide 100' is then removed by sliding the drill guide along the previously placed K-wires and away from the surface of the bone.

Next, as shown in FIG. 15, a cannulated inserter/impactor 140', configured for use in addressing fractures of the dorsal rim of the distal radius, is secured to dorsal hook plate 300. Specifically, a hexalobular or other suitable driver is employed to rotate cannulated set screw 170 clockwise, advancing the set screw through flange 168' of base 160', causing the set screw's threads to engage cooperating threads of peg hole 330 of bone plate 300. This affixation may be simplified by providing a caddy having an assembly slot within an overall tray of hook plates, cannulated drill guides, cannulated inserters/impactors, cannulated set screws, K-wires, fasteners, and other implements, supplied as an overall kit for performing the present surgical procedure.

Upon attachment of inserter/impactor 140' to a hook plate 300 via the threaded engagement of set screw 170 with locking peg hole 330, curvilinear bottom surface 164' of inserter/impactor base 160' is configured to substantially match the adjacent top surface contours of, and to rest directly atop, a distal portion of hook plate 300, with the apex of hook members 304 and 305 adjacent an arcuate portion of bottom surface 164', and with a longitudinal axis of inserter/impactor 140' being parallel to and proximate to the longitudinal axes of hook members 304 and 305. This, in turn, transfers a striking force applied to the top surface of inserter/impactor 140' in a direction substantially along the length of both hook members 304 and 305 of attached hook plate 300, to facilitate impacting the hook members into previously drilled pilot holes into one or more bone fragments proximate the fracture site. Moreover, with reference to FIG. 15, the longitudinal axis of flange 168' is disposed at an angle relative to the longitudinal axis of handle 150' that substantially coincides with the angle between the flared region and hook members 304 and 305 of bone plate 300. This, in turn, further enables the parallel alignment of a longitudinal axis of handle 150 with the longitudinal axes of hook members 304 and 305 of bone plate 300.

As shown in FIG. 15, the cannula, or longitudinal central channel of base 160' of inserter/impactor 140' is positioned to engage and is then advanced along distal K-wire 10, with hook members 304 and 305 of dorsal hook plate 300 being guided into the associated pilot holes, and with the additional K-wires 10, if present, further guiding the edge of the hook plate, proximally, until hook plate 300 is fully seated, with a bottom surface of hook plate 300 positioned adjacent the bone and across the fracture site. A hammer may be applied to the striking surface of handle 150' to fully seat dorsal hook plate 300, as shown in FIG. 16.

Figure 17:
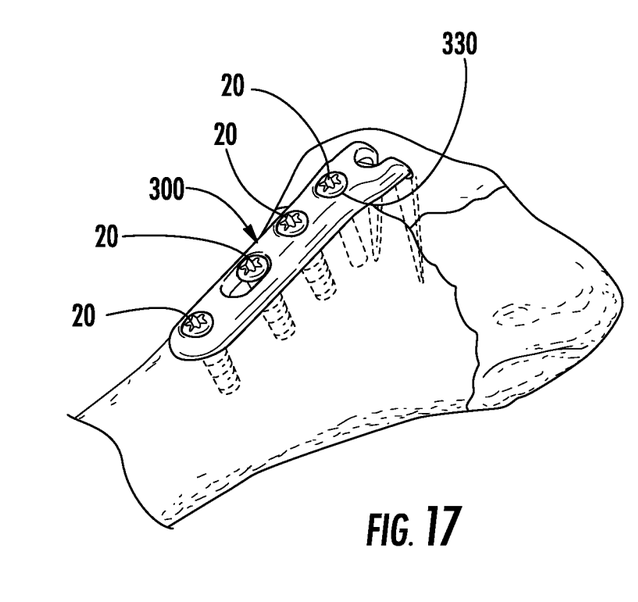
FIG. 17 is a top perspective view of the fracture fixation plate of FIGS. 15 and 16, showing complete fixation of a fracture of the distal dorsal rim.

Next, a 2.3 millimeter screw 20 is placed through the proximal slotted hole of hook plate 300 and into the adjacent bone to secure hook plate 300 proximally. Handle 150' is then unscrewed and removed from base 160' of inserter/impactor 140', and the distal K-wire is likewise removed. A hole is then drilled for a distal subchondral locking peg by advancing a suitably sized drill bit through the cannula, or longitudinal channel, of set screw 170 and into the adjacent bone, between the intra-osseous tines of hook plate 300. Base 160' is then removed by rotating cannulated set screw 170 counterclockwise to disengage the threads of set screw 170 from peg hole 330 of bone plate 300. As shown in FIG. 17, proximal fixation is then completed using additional 2.3 millimeter cortical screws 20 or 2.3 millimeter threaded locking pegs. Depending upon the type and severity of the fracture, additional dorsal and/or volar hook plates may be applied in a similar manner, as needed.

Each of cannulated double barreled drill guides 100 and 100' and cannulated inserter/impactors 140 and 140' may be constructed of a surgical stainless steel material, such as, for example, type 17-4 precipitation hardened surgical stainless steel, condition H-900. Cannulated set screw 170 may likewise be constructed of a surgical stainless steel material, such as, for example, type 455/465 precipitation hardened surgical stainless steel, condition H-900. The implants, guides, and inserter components may be alternatively manufactured from other suitable surgical grade materials The preceding description and drawings merely explain the invention and the invention is not limited thereto, as those of ordinary skill in the art who have the present disclosure before them will be able to make changes and variations thereto without departing from the scope of the present invention.

What is claimed is:

1. A system for inserting a bone plate into a predetermined location of a bone having a contoured surface, the system comprising:
    a bone plate having a body with a predominant central longitudinal axis, a contoured bottom surface, and at least two hook shaped members for insertion into at least two parallel pilot holes predrilled into the bone, each of the pilot holes having an entry point, the at least two hook shaped members each having a longitudinal axis that is parallel to the other, each of the at least two hook shaped members being in a fixed positional relationship relative to each other, each of the two hook shaped members being in a fixed longitudinal position relative to the body of the bone plate, and each of the two hook shaped members being in a fixed lateral position to the predominant central longitudinal axis of the body of the bone plate;
    a guide pin having a longitudinal axis, a portion of the guide pin being placeable into the bone at a specific location and angular trajectory to reference an intended final position and orientation of the bone plate relative to the bone;
    a drill guide facilitating drilling the at least two parallel pilot holes in the bone at a predetermined fixed spatial position and predetermined fixed angular orientation in reference to the orientation and insertional position of the guide pin, the drill guide having a first guide pin channel sized to permit passage of the guide pin therethrough while constraining lateral movement of the drill guide relative to the guide pin;
    the drill guide further having at least two drill guide channels for drilling the pilot holes, the at least two drill guide channels being substantially parallel to each other and spaced apart from each other by a distance substantially coinciding with a relative spacing of the longitudinal axes of the at least two hook shaped members, wherein the first guide pin channel having a fixed spatial relationship and fixed angular orientation relative to each of the at least two drill guide channels; and
    an impactable instrument rigidly and releasably attachable to the bone plate, the impactable instrument having a second guide pin channel extending through at least a portion of the impactable instrument, the second guide pin channel being sized to permit passage of the guide pin therethrough while constraining lateral movement of the impactable instrument relative to the guide pin,
    such that with the impactable instrument is securely attached to the bone plate and the guide pin is positioned in the bone at the reference location and extending through the second guide pin channel, the at least two hook shaped members are urged to substantially align with the longitudinal axis of the guide pin and the corresponding entry points and longitudinal axes of the pilot holes to guide the hook shaped members to be impacted into the predetermined location of the bone and result in coaptation of the contoured bottom surface of the bone plate with the contoured surface of the bone.

2. The system according to claim 1, wherein, upon attachment of the impactable instrument to the bone plate, the impactable instrument is not in contact with any surface portion of the bone plate that will, in turn, be in contact with the bone upon the implanting of the bone plate.

3. The system according to claim 1, further comprising a fastener securely coupling the impactable instrument to the bone plate.

4. The system according to claim 3, wherein the fastener securely coupling the impactable instrument to the bone plate is a cannulated fastener, permitting a pilot hole for a locking fastener to be drilled by advancing a drill bit through both the cannulated fastener and an aperture of the bone plate and into adjacent bone when the cannulated fastener is securely coupled to both the bone plate and the impactable instrument.

5. The system according to claim 3, wherein, upon attachment of the impactable instrument to the bone plate, the fastener is coupled to an aperture that is disposed through the body of the bone plate and that is positioned to permit a locking fastener to be placed though the aperture and into the bone along an extended axis intersecting a plane joining longitudinal axes of the at least two hook shaped members of the bone plate.

6. The system according to claim 1, wherein the impactable instrument further includes a detachable handle.

7. The system according to claim 6, wherein the detachable handle includes a top impactable surface and an open interior region in communication with the second guide pin channel of the impactable instrument upon attachment of the detachable handle to the impactable instrument.

8. The system according to claim 1, wherein a bottom surface of the impactable instrument has a surface contour substantially matching a top surface contour of an adjacent portion of the bone plate upon attachment of the impactable instrument to the bone plate.

9. The system according to claim 1, wherein:
the body of the bone plate includes a predominantly longitudinal axis and a contoured bottom surface, with at least two of the hook shaped members each having a predominantly longitudinal axis disposed at a first angle relative to the predominantly longitudinal axis of the body of the bone plate;
the body of the drill guide includes a predominantly longitudinal axis and a contoured bottom surface, and at least two of the drill guide channels each have a predominantly longitudinal axis extending therethrough and disposed at a second angle relative to the predominantly longitudinal axis of the body of the drill guide;
at least a first portion of the contoured bottom surface of the bone plate substantially matching in contour a corresponding first portion of the contoured bottom surface of the drill guide;
the first angle and the second angle being substantially equal to each other; and
the predominantly longitudinal axes of the drill guide channels each being spaced and oriented relative to the first portion of the contoured bottom surface of the drill guide in a manner substantially equal to a spacing and orientation of a corresponding one of the predominantly longitudinal axes of the hook shaped members relative to the matching first portion of the contoured bottom surface of the bone plate.

10. The system according to claim 1, wherein at least one of the drill guide channels has a predominantly longitudinal axis extending therethrough that is disposed at an angle relative to a predominantly longitudinal axis of a flared region of the body of the drill guide that substantially corresponds to an angle between a predominantly longitudinal axis of at least one of the at least two hook shaped members of the bone plate and a predominantly longitudinal axis of an adjacent, flared region of the body of the bone plate.

11. A method for inserting a bone plate into a predetermined location of a bone having a contoured surface, the method comprising the steps of:
providing a bone plate having a body with a contoured bottom surface and a predominant central longitudinal axis and at least two hook shaped members for insertion into at least two parallel pilot holes predrilled into the bone, each of the pilot holes having an entry point, the at least two hook shaped members each having a longitudinal axis that is parallel to the other, each of the at least two hook shaped members being in a fixed positional relationship relative to each other and to, each of the two hook shaped members being in a fixed longitudinal position relative to the body of the bone plate, and each of the two hook shaped members being in a fixed lateral position to the predominant central longitudinal axis of the body of the bone plate;
placing a portion of a guide pin having a longitudinal axis into the bone at a specific location and angular trajectory to reference an intended final position and orientation of the bone plate relative to the bone;
providing a drill guide facilitating drilling the at least two parallel pilot holes in the bone at a predetermined fixed spatial position and predetermined fixed angular orientation in reference to the orientation and insertional position of the guide pin, the drill guide having a first guide pin channel sized to permit passage of the guide pin therethrough while constraining lateral movement of the drill guide relative to the guide pin, the drill guide further having at least two drill guide channels for drilling the pilot holes, the at least two drill guide channels being substantially parallel to each other and spaced apart from each other by a distance substantially coinciding with a relative spacing of the longitudinal axes of the at least two hook shaped members, wherein the first guide pin channel has a fixed spatial relationship and fixed angular orientation relative to each of the at least two drill guide channels;
advancing the first guide pin of the drill guide along the guide pin until the at least two drill guide channels come into proximity with the bone at the predetermined location;
advancing a drill bit through each of the at least two drill guide channels to drill each of the at least two pilot holes;
removing the drill guide and the first guide pin channel from the guide pin by drawing the drill guide away from the bone;
providing an impactable instrument rigidly and releasably attachable to the bone plate, the impactable instrument having a second guide pin channel extending through at least a portion of the impactable instrument, the second guide pin channel being sized to permit passage of the guide pin therethrough while constraining lateral movement of the impactable instrument relative to the guide pin,
securely attaching the impactable instrument to the bone plate; and
advancing the second guide pin channel of the impactable instrument along the longitudinal axis of the guide pin to urge the longitudinal axes of the hook shaped members into substantial alignment with the longitudinal axis of the guide pin and the corresponding entry points and longitudinal axes of the pilot holes to guide the hook shaped members to be impacted at the predetermined location of the bone and result in coaptation of the contoured surface of the bone plate with the contoured bottom surface of the bone.

12. The method according to claim 11, further comprising the step of striking an impactable surface region of the impactable instrument to, in turn, advance each of the at least two hook shaped members into corresponding pilot holes.

13. The method according to claim 12, further comprising the step of detaching the impactable instrument from the bone plate following the advancement of each of the at least two hook shaped members into corresponding pilot holes.

* * * * *